US008012973B2

(12) United States Patent
Fernández et al.

(10) Patent No.: US 8,012,973 B2
(45) Date of Patent: Sep. 6, 2011

(54) COMPOUNDS FOR THE TREATMENT OF AURICULAR FIBRILLATION

(75) Inventors: Rafael Franco Fernández, Barcelona (ES); Franciso Ciruela Alférez, Barcelona (ES); Carmen Lluís Biset, Barcelona (ES); Christa Müller, Bonn (DE); Joan Cinca Cuscullola, Barcelona (ES); Leif Hove-Madsen, Tiana Barcelona (ES)

(73) Assignee: Proyecto de Biomedicina Cima S.L., Navarre (ES)

( * ) Notice: Subject to any disclaimer, the term of this patent is extended or adjusted under 35 U.S.C. 154(b) by 353 days.

(21) Appl. No.: 12/090,115

(22) PCT Filed: Oct. 10, 2006

(86) PCT No.: PCT/ES2006/000564
§ 371 (c)(1),
(2), (4) Date: Aug. 26, 2008

(87) PCT Pub. No.: WO2007/045705
PCT Pub. Date: Apr. 26, 2007

(65) Prior Publication Data
US 2009/0312332 A1     Dec. 17, 2009

(30) Foreign Application Priority Data

Oct. 14, 2005    (ES) .................................. 200502545

(51) Int. Cl.
*A61K 31/519* (2006.01)
*A61K 31/53* (2006.01)
*A61K 31/4985* (2006.01)
*A61K 31/522* (2006.01)
(52) U.S. Cl. .................. 514/245; 514/249; 514/259.31; 514/260.1; 514/263.34; 514/267
(58) Field of Classification Search .................. 514/245, 514/249, 259.31, 260.1, 263.34, 267
See application file for complete search history.

(56) References Cited

U.S. PATENT DOCUMENTS

| 4,772,607 | A | | 9/1988 | Badger et al. |
| 4,780,464 | A | * | 10/1988 | Trivedi ........................ 514/250 |
| 5,998,387 | A | | 12/1999 | Belardinelli et al. |
| 6,051,578 | A | * | 4/2000 | Chen ........................ 514/262.1 |
| 6,060,478 | A | * | 5/2000 | Gilligan et al. ............ 514/228.5 |
| 2003/0022890 | A1 | | 1/2003 | Atwal et al. |
| 2004/0192698 | A1 | | 9/2004 | Benbow et al. |

FOREIGN PATENT DOCUMENTS

| EP | 544444 A1 | 11/1992 |
| WO | 01/40425 A2 | 6/2001 |
| WO | 02/055524 A1 | 7/2002 |

OTHER PUBLICATIONS

Patani et al., Bioisosterism: A Rational Approach in Drug Design, 1996, Chem. Rev., 96, 3147-3176.*
Bertolet, Barry D., et al., Myocardial infarction related atrial fibrillation: role of endogenous adenosine, Heart, 1997, pp. 88-90, vol. 78.
Iqbal, M Bilal, et al., Recent developments in atrial fibrillation, BJM, Jan. 29, 2005, pp. 238-243, vol. 330.
Bertolet, Barry D., et al., "Myocardial infarction related atrial fibrillation role of endogenous adenosine", Heart, 78:88-90 (1997).
Jacobson, Kenneth A. et al., "Adenosine receptors as therapeutic targets", Nature Reviews: Drug Discovery, 5:247-264 (Mar. 2006).

* cited by examiner

*Primary Examiner* — James Anderson
*Assistant Examiner* — Zohreh Vakili
(74) *Attorney, Agent, or Firm* — Tristan A. Fuierer; Andy Gerschutz; Moore & Van Allen, PLLC

(57) ABSTRACT

Adenosine $A_{2A}$ receptor antagonists are useful for the preparation of medicaments against atrial fibrillation in mammals, including humans. It has been found that the adenosine $A_{2A}$ receptor is present in human atrial cardiomyocytes and participates in the pathological mechanisms underlying atrial fibrillation. An advantage of using $A_{2A}$ antagonists over other agents known in the art is that the $A_{2A}$ antagonists specifically target patients with atrial fibrillation.

8 Claims, 5 Drawing Sheets

Control        50 nM SCH        W

COMPOUNDS FOR THE TREATMENT OF AURICULAR FIBRILLATION

CROSS-REFERENCE TO RELATED APPLICATIONS

This application is filed under the provisions of 35 U.S.C. §371 and claims the priority of International Patent Application No. PCT/ES2006/000564 filed on 10 Oct. 2006 entitled "Compounds for the Treatment of Auricular Fibrillation" in the name of Franco Fernández, Rafael et al., which in turn claims priority of Application No. P200502545 (ES) filed on 14 Oct. 2005, all copies of which are hereby incorporated by reference herein in their entirety.

This invention relates to the field of human and veterinarian medicine and specifically to compounds for the treatment of cardiovascular diseases, in particular for the treatment of atrial fibrillation.

BACKGROUND ART

Atrial fibrillation is the most common cardiac arrhythmia and is associated with substantial morbidity and mortality. Its incidence and prevalence are increasing and it represents a growing clinical and economic burden (current prevalence is of 2% in the general population). In addition to severe clinical symptoms like palpitations, dizziness, dyspnea and others, atrial fibrillation is the single most important factor for ischemic stroke in the population over 75 years of age. Overall, atrial fibrillation accounts for over 5% of hospital admissions for cardiovascular diseases. In about 90% of cases atrial fibrillation occurs in the presence of other cardiac diseases, like hypertensive heart disease, congestive heart failure or cardiac valve diseases. In only 10% of cases does atrial fibrillation develop in the absence of cardiac abnormalities ("lone" atrial fibrillation). Three forms of atrial fibrillation can be differentiated: (1) paroxysmal atrial fibrillation characterized by self-terminating atrial fibrillation episodes with durations that vary from seconds to days; (2) persistent atrial fibrillation that lasts indefinitely until terminated by medical interventions; (3) permanent atrial fibrillation that cannot be terminated by pharmacological or electrical cardioversion.

Studies have shown that atrial fibrillation results from multiple re-entrant electrical wavelets that move randomly around the atria. These wavelets are initiated by electrical triggers, commonly located in the myocardial sleeves extending from the left atrium to the proximal 5-6 cm portions of the pulmonary veins. Once atrial fibrillation is triggered, changes in the atria are produced (atria remodelling) which affect to its electrical, mechanical and metabolic properties, responsible of arrhythmia persistence. Ventricular rate control in presence of atrial fibrillation is elevated and if rate control can not be reduced with medical treatment, leads to ventricular dilatation and impairment of systolic function, commonly referred to as tachycardiomyopathy. Stroke and thromboembolism are a major cause of mortality and morbidity associated with atrial fibrillation, and the underlying pathophysiological basis of this is a prothrombotic or hypercoagulable state in association with abnormalities of blood flow (atrial stasis, for example) and endothelial or endocardial damage.

As in other subspecialties in cardiology, important progress has been made in the diagnosis and treatment of cardiac arrhythmias during the last four decades. In spite of many advances, a really cure of cardiac arrhythmias and the prevention of sudden arrhythmic death is in a minority of the patients. Nowadays atrial fibrillation therapy encompasses the reduction of atrial fibrillation-related symptoms, prevention of thromboembolic complications, and termination of the arrhythmia when appropriate.

In general there are two approaches in the management of atrial fibrillation: a) management of the arrhythmia itself and b) reduction of the thromboembolic risk (cf. M. B. Iqbal et al., "Recent developments in atrial fibrillation", *British Medical Journal* 2005, vol. 330, pp. 238-43). Management of the arrhythmia encompasses rhythm control (restoration and maintenance of sinus rhythm) and rate control. Pharmacologically, rhythm and rate control are managed with antiarrhythmic drugs (class I and class III antiarrhythmic agents). Examples of them which are used nowadays are flecainide, propafenone, amiodarone, dofetilide, ibutilide and sotalol. Non-pharmacologically, rhythm and rate control are managed with electrical cardioversion, atrial based pacing, implantable atrial defibrillator, radiofrequency catheter ablation and surgical maze procedure.

Reduction of the thromboembolic risk and thus, stroke prevention are of major importance in treatment strategy. Pharmacologically, aspirin and warfarin are recommended in the majority of patients to prevent atrial thrombus formation and thromboembolic events. Pooled data from trials with high risk patients show that warfarin is better than aspirin in preventing strokes, but the risk of major haemorrhage with warfarin is twice that with aspirin. Anyway, anticoagulation treatment needs to be tailored individually on the basis of age, comorbidities and contraindications. Non-pharmacologically, reduction of the thromboembolic risk is currently managed with obliteration of left atrial appendage or with catheter (procedure under research).

Recent research has highlighted new approaches to both pharmacological and non-pharmacological management strategies. The most promising agents are angiotensin converting enzyme (ACE) inhibitors and angiotensin II receptor blocking drugs. Protease inhibitors, phosphatases of sufficient selectivity and specificity or antioxidants may also offer novel therapeutic strategies to reduce or reverse structural changes, atrial dilation, and contractile dysfunction. However, the problem of treatment of atrial fibrillation is still far from being solved satisfactorily.

SUMMARY OF THE INVENTION

Inventors have found that a well-known group of pharmaceutical compounds, namely the adenosine $A_{2A}$ receptor antagonists, are useful for the preparation of medicaments against atrial fibrillation in mammals, including humans.

The invention has been originated from the surprising finding that the adenosine $A_{2A}$ receptor is present in human atrial cardiomyocytes and participates in the pathological mechanisms underlying atrial fibrillation. Particularly, the inventors have found that the expression of the homodimeric adenosine $A_{2A}$ receptor species, which is the functional species in the plasma membrane, is up-regulated in patients with atrial fibrillation. Electrophysiological experiments have proved that activation of adenosine $A_{2A}$ receptor in atrial myocytes from these patients leads to protein kinase A-mediated increases in spontaneous sarcoplasmic reticulum calcium release measured as calcium waves.

Moreover, using two different experimental approaches (confocal calcium imaging and patch clamp technique) the inventors have found that adenosine $A_{2A}$ receptor antagonists reduced the elevated calcium wave frequency found in atrial fibrillation. Indeed, adenosine $A_{2A}$ receptor antagonists not only reverse the agonist stimulatory effect on calcium waves but also reduce the basal calcium wave frequency. Taken together, these results suggest that an adenosine $A_{2A}$ receptor-mediated dysregulation of intracellular calcium fluxes contributes to the complex electrical remodelling of the fibrillating atrium. These facts turn adenosine $A_{2A}$ receptor antagonists into selective therapeutic agents to treat atrial fibrillation.

Previously, and as a closest research study, the inventors had only described that isolated right atrial myocytes from patients with episodes of atrial fibrillation exhibit a more frequent spontaneous sarcoplasmic reticulum $Ca^{2+}$ release than myocytes from patients free of this arrhythmia (cf. L. Hove-Madsen et al., "Atrial fibrillation is associated with increased spontaneous calcium release from the sarcoplasmic reticulum in human atrial myocytes", *Circulation* 2004, vol. September, pp. 1358-63).

Accordingly, the present invention relates to the use of an adenosine $A_{2A}$ receptor antagonist for the preparation of a medicament for prevention and/or treatment of atrial fibrillation in a mammal, including a human. Hereafter "adenosine $A_{2A}$ receptor antagonist" will be called as "$A_{2A}$ antagonist" and "adenosine $A_{2A}$ receptor" as "$A_{2A}$ receptor". This aspect of the invention may alternatively be formulated as a method for prevention and/or treatment of atrial fibrillation by antagonizing $A_{2A}$ receptors, which comprises administering to a mammal (preferably a human) in need thereof an effective amount of an $A_{2A}$ antagonist together with appropriate amounts of acceptable diluents or carriers.

An advantage of using $A_{2A}$ antagonists over other agents known in the art is that the $A_{2A}$ antagonists specifically target patients with atrial fibrillation. Thus, the expression of functional dimeric $A_{2A}$ receptors is low in patients with normal atrial size and without a previous history of atrial fibrillation while the expression of the dimeric receptor species is strongly upregulated in patients with atrial fibrillation. On the contrary, other agents currently employed act more broadly on receptors or channels that critically regulate multiple functions in a variety of cells. Thus, calcium antagonists will not only reduce calcium overload by inhibiting L-type calcium channels, but also reduce cardiac contractility. Moreover, L-type calcium current also regulates smooth muscle function and secretory cells, with undesired side effects of calcium antagonists as a consequence.

$A_{2A}$ Receptor

Adenosine is a purine nucleoside produced by all metabolically active cells within the body. Adenosine exerts its effects through four identified different subtypes of cell-surface receptor: $A_1$, $A_{2A}$, $A_{2B}$ and $A_3$ which belong to the G protein coupled receptor superfamily. $A_1$ and $A_3$ couple to inhibitory G protein, while $A_{2A}$ and $A_{2B}$ couple to stimulatory G protein. $A_{2A}$ receptors are mainly found in brain, both in neurons and glial cells (highest level in the striatum and nucleus accumbens, moderate to high level in olfactory bulb and hypothalamus and hippocampus regions). In striatum the $A_{2A}$ receptor regulates the release and the function of neurotransmitters (cf. H. Kase et al. "Progress in pursuit of therapeutic $A_{2A}$ antagonists: the adenosine $A_{2A}$ receptor selective antagonist KW 6002: research and development toward a novel nondopaminergic therapy for Parkinson's disease", *Neurology* 2003, vol. 61, pp. 97-100). In peripheral tissues, $A_{2A}$ receptors are known to be present in platelets, neutrophils, spleen, thymus, endothelium and vascular smooth muscle cells, where induce a potent coronary vasodilatation which permits assessment of myocardial perfusion in patients with coronary heart disease (cf. Z. Gao et al., "Novel short-acting $A_{2A}$ adenosine receptor agonists for coronary vasodilatation: inverse relationship between affinity and duration of action of $A_{2A}$ agonists", *J. Pharmacol. Exp. Ther.* 2001, vol. 298, pp. 209-18). However, $A_{2A}$ receptor has never been localized, until now, in human atrial cardiomyocytes.

Suitable Compounds to Treat Atrial Fibrillation

In general, an antagonist is a molecule that binds to the receptor without activating the receptor. It competes with the endogenous ligand(s) or substrate(s) for binding site(s) on the receptor and thus, inhibits the ability of the receptor to transduce an intracellular signal in response to endogenous ligand binding. An antagonist functions in several ways. It may bind to or sequester adenosine with sufficient affinity and specificity to substantially interfere with, block or otherwise prevent binding of adenosine to the $A_{2A}$ receptor, thereby inhibiting, suppressing or causing the cessation of the adenosine-mediated biological activity.

$A_{2A}$ receptor in cardiomyocytes and in absence of endogenous ligand, presents a basal activity. This activity can be due to constitutive activity of the receptor or by activation of the receptor by endogenous adenosine. In this situation, treatment of atrial fibrillation can be achieved by reducing this basal activity by using an antagonist or an inverse agonist. Some of the $A_{2A}$ antagonists of the invention can display inverse agonism.

According to the known localization and function of the $A_{2A}$ receptor, $A_{2A}$ antagonists have been used until now against Parkinson and other diseases of the CNS (schizophrenia, senile dementia as in Alzheimer's disease, psychoses of organic origin, etc.). Among them the main one is Parkinson's disease.

Every $A_{2A}$ antagonist is contemplated for use for the purposes of this invention. Many different compounds have been deeply investigated as $A_{2A}$ antagonists, which could be classified in two great families: xanthine derivatives and non-xanthine heterocycles.

In a particular embodiment of the invention, the $A_{2A}$ antagonist is a xanthine derivative or a pharmaceutically acceptable salt thereof. Different substituents in the various positions, also deazo- or azo-analogs or other heterocyclic analogs of the purine ring or tri- or tetracyclic derivatives/analogs, can have similar $A_{2A}$-antagonistic activity. Among xanthine derivatives, the preferred structure common to some compounds is the 1,3,7-trialkyl-8-styryl-xanthine structure. In a preferred embodiment, the $A_{2A}$ antagonist is a compound selected from the group consisting of theobromine, known as DMPX (formula 1); KF 17837 (formula 2); istradefylline, known as KW 6002 (formula 3); p-sulfostyryl-DMPX (formula 4); BS-DMPX (formula 5); MSX-2 (formula 6); CSC (formula 7); xanthine amine congener (XAC, formula 8); and MSX-3.

In a more preferred embodiment, the $A_{2A}$ antagonist is KW 6002. This compound is now under clinical trials of phase III for Parkinson's disease. In another preferred embodiment, the $A_{2A}$ antagonist is MSX-2. In another preferred embodiment, the $A_{2A}$ antagonist is MSX-3, the phosphoric acid ester of MSX-2, a prodrug of MSX-2.

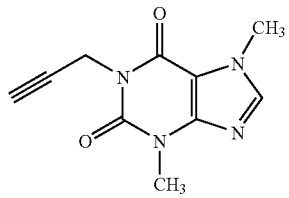

(1)

(2)
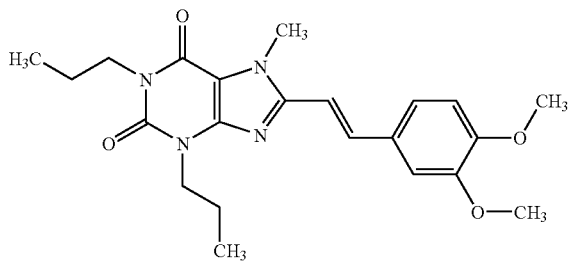

(3)
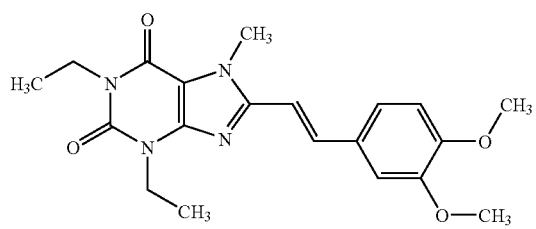

(4)
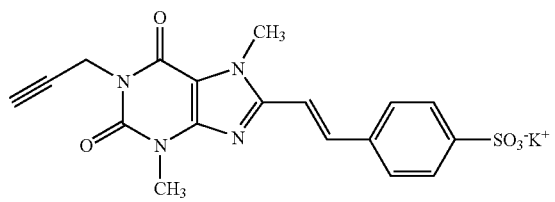

(5)
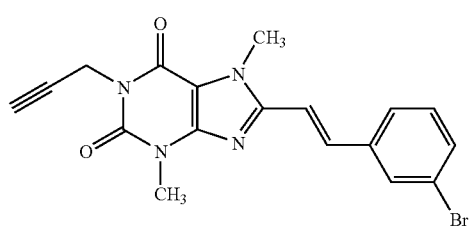

(6)
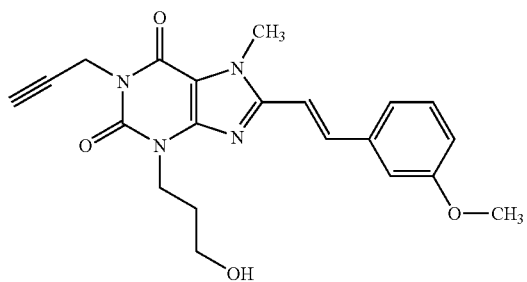

(7)
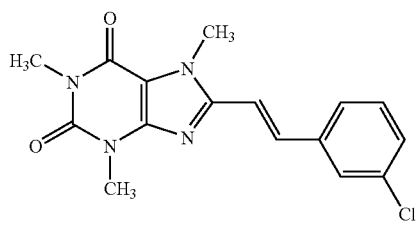

(8)
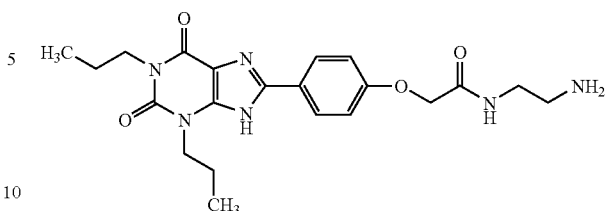

Other xanthine compounds known to show $A_{2A}$ receptor antagonistic activity are described in for instance U.S. Pat. Nos. 5,484,920, 5,587,378, 5,543,415 and EP 1016407A1.

In another particular embodiment of the invention, the $A_{2A}$ antagonist is a non-xanthine heterocycle. Typical non-xanthine adenosine $A_{2A}$ antagonists may be derived from adenine and represent adenine derivatives in the widest sense, including mono-, di-, tri- and tetracyclic compounds bearing various substituents. Further heterocyclic compounds, not derived from adenine have been identified that possess $A_{2A}$-antagonistic activity. Some 2-aminopyridine compounds to exhibit $A_{2A}$ receptor antagonism are known (e.g. WO 02/14282, WO 01/25210), and some 9-aminopyrimidine compounds are also known (e.g. US 2001/0027196).

In a preferred embodiment, the $A_{2A}$ antagonist is selected from the group consisting of SCH 58261 (formula 9); ANR-82 (formula 10); ZM 241385 (formula 11); SCH 63390 (formula 12), CGS 15943 (formula 13), 8FB-PTP (formula 14); VER-6623 (also known as V2006, formula 15); (−)R,S-mefloquine (formula 16); and 7FB-PTP (formula 17). In a more preferred embodiment, the $A_{2A}$ antagonist among the group of non-xanthine compounds is VER-6623.

Other compounds preferred as $A_{2A}$ antagonists are the pyrazolopyrimidine derivative of formula 18; the triazoloquinoxaline derivative of formula 19; the 9-substituted 2-amino-6-furyl-adenine derivative of formula 20; and the triazolotriazine derivatives of formula 21, 22 and 23.

(9)
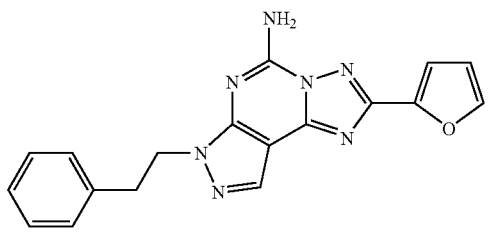

(10)
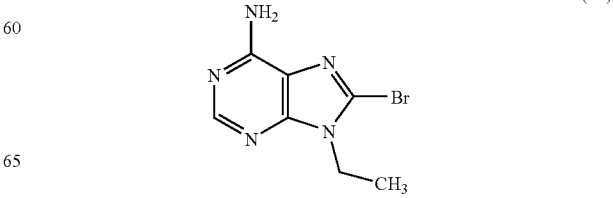

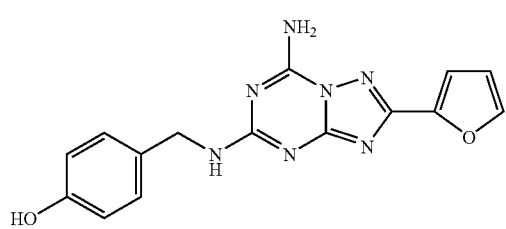
(11)
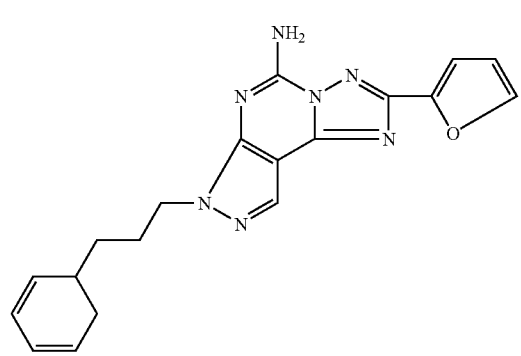
(12)
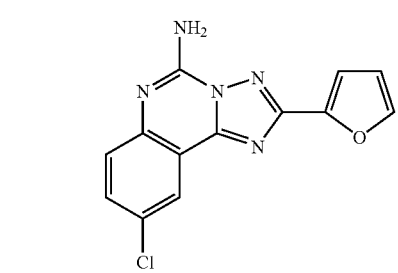
(13)
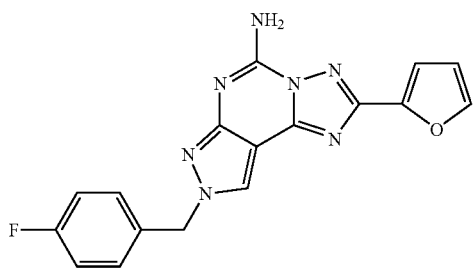
(14)
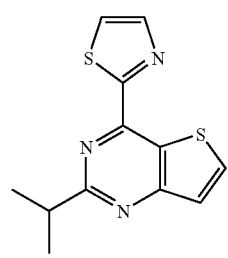
(15)
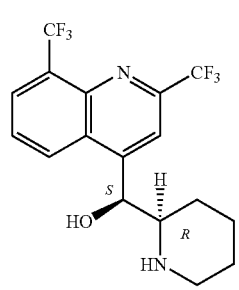
(16)
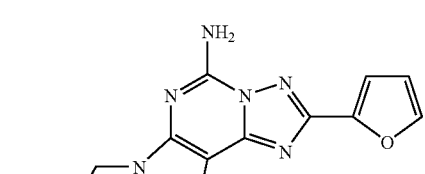
(17)
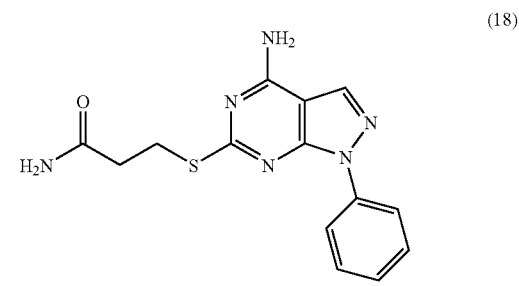
(18)
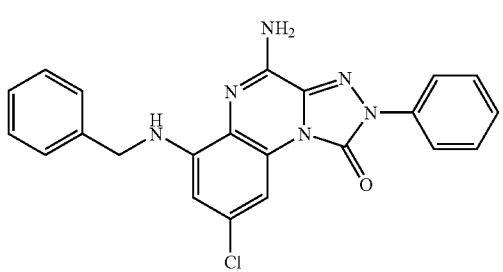
(19)
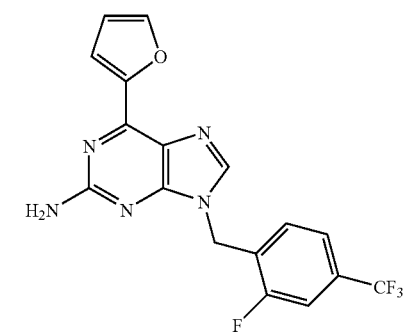
(20)
(21)

-continued (22)

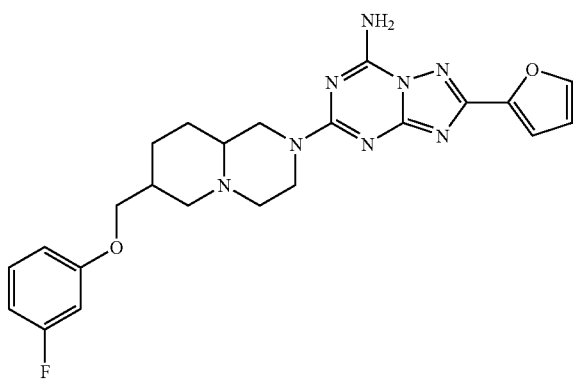

(23)

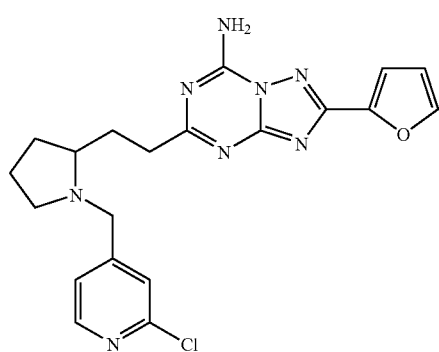

Other triazolopyrimidine $A_{2A}$ antagonists are disclosed for example in WO 2004/029056, WO 95/01356, U.S. Pat. No. 5,565,460, WO 97/05138, WO 98/52568, WO 01/92264 and PCT/US02/32630. Specifically, substituted pyrazol[4,3-e]-1, 2,4-triazolo-[1,5-c]pyrimidine compounds are disclosed in WO 2005/054245, US 2004/220194 and US 2003212059.

Other specific examples of suitable $A_{2A}$ antagonists include the compounds disclosed in the following patents, patent applications and articles: WO 95/01356, U.S. Pat. Nos. 6,630,475, 5,935,964, WO 03/032996, WO 03/048165, WO 03/048164, WO 03/048163, WO 2005/042500, WO 2005/058883, WO 2005/040151, WO 2005/039572, WO 2004/092177, US 2004138235, WO 2004/019949, WO 02/14282, WO 2004/016605, WO 03/082873, U.S. Pat. Nos. 5,484,920, 5,703,085, WO 92/06976, WO 94/01114, U.S. Pat. No. 5,565,460, WO 98/42711, WO 00/7201, WO 99/43678, WO 99/26627, WO 01/92264, WO 99/35147, WO 00/13682, WO 00/13681, WO 00/69464, WO 01/40230, WO 01/02409, WO 01/02400, EP 1054012, WO 01/62233, WO 01/17999, WO 01/80893, WO 02/14282, WO 01/97786, WO 01/16134, WO 00/73307, US 2005043315, US 2003149060, Baraldi et al., "Recent developments in the field of $A_{2A}$ and $A_3$ adenosine receptor antagonists", *European Journal of Medicinal Chemistry* 2003, vol. 38, pp. 367-82; E. Ongini, et al. "Selective adenosine $A_{2A}$ receptor antagonists", *Farmaco* 2001, vol. 56, pp. 87-90; C. E. Müller et al., "$A_{2A}$ Adenosine receptor antagonists—future drugs for Parkinson's disease?", *Drugs of the Future* 2000, vol. 25, pp. 1043-52; L. J. Knutsen et al., "KW-6002 (Kyowa Hakko Kogyo)", *Curr. Opin. Investig. Drugs* 2001, vol. 2, pp. 668-73; B. Cacciari et al., "Medicinal chemistry of $A_{2A}$ adenosine receptor antagonists", *Curr. Top. Med. Chem.* 2003, vol. 3, pp. 403-11; G. Yao et al., "Synthesis of alkyne derivatives of novel triazolopyrazine as $A_{2A}$ adenosine receptor antagonists", *Bioorg. Med. Chem. Lett.* 2005, vol. 15, pp. 511-5; E. Kiselgof et al., "6-(2-furanyl)-9H-purin-2-amine derivatives as $A_{2A}$ adenosine antagonists", *Bioorg. Med. Chem. Lett.* 2005, vol. 15, pp. 2119-22; S. M. Weiss et al., "Discovery of nonxanthine adenosine $A_{2A}$ receptor antagonists for the treatment of Parkinson's disease", *Neurology* 2003, vol. 61 (Supp. 6), pp. S101-6; C. B. Vu et al., "Novel diamino derivatives of [1,24]triazolo[1,5-a][1,3,5]triazine as potent and selective adenosine $A_{2A}$ receptor antagonists", *J. Med. Chem.* 2005, vol. 48, pp. 2009-18; C. B. Vu et al., "piperazine derivatives of [1,2,4]triazolo[1,5-a][1,3,5]triazine as potent and selective adenosine $A_{2A}$ receptor antagonists", *J. Med. Chem.* 2004, vol. 47, pp. 4291-9.

The person skilled in the art will know whether a compound is a good $A_{2A}$ antagonist for the purpose of the invention. For instance, there are in the art suitable methods to assess whether a compound is a good $A_{2A}$ antagonist. An example is the method based on a radioligand binding assay described in the patent application US 2004/0138235 sections [0226]-[0240].

It is preferred for the treatment of atrial fibrillation that the $A_{2A}$ antagonist is selective for $A_{2A}$ receptor. All the $A_{2A}$ antagonists described above are selective for the $A_{2A}$ receptor, but the degree of selectivity is different among them. The selectivities may also differ somewhat among different species (e.g. rat, human).

The $A_{2A}$ antagonists are prepared by known methods as described in the cited patents and applications.

Pharmaceutical Compositions and Administration

In terms of treatment, an effective amount refers to that amount of the active ingredient that is sufficient to affect a beneficial or desired clinical result: to palliate, ameliorate, stabilize, reverse or slow the progression of the disease or disorder, or otherwise reduce the pathological consequences of the disease or disorder. The effective amount is generally determined by the physician on a case-by-case basis.

While the active compound for use according to the invention in therapy may be administered in the form of raw chemical compound, it is preferred to introduce the active ingredient, optionally in the form of physiologically acceptable salt, in a pharmaceutical composition together with one or more adjuvants, excipients, carriers, buffers, diluents and/or other customary pharmaceutical auxiliaries. The components may be administered in either single or multiple doses by any of the accepted modes of administration of agents having similar utilities, including rectal, buccal, intranasal and transdermal routes, by intra-arterial injection, intravenously, intraperitonealy, parenterally, intramuscularly, subcutaneously, orally, topically, as an inhalant, or via an impregnated or coated device such as a stent, for example, or an artery-inserted cylindrical polymer.

One preferred mode for administration is parental, particularly by injection. The forms for administration by injection include aqueous or oil suspensions, or emulsions, as well as sterile aqueous solutions. Oral administration is another preferred route for administration. The pharmaceutical composition can be in the form of tablets, pills, powders, elixirs, suspensions, emulsions, solutions, syrups, aerosols, capsules, etc.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Another formulation for use in the methods of the present invention employs transdermal delivery devices ("patches"). Such transdermal patches may be used to provide continuous or discontinuous infusion of the compounds in controlled amounts.

The compositions are preferably formulated in a unit dosage form. The dosage depends on the nature and severity of the disease, and its determination is within the discretion of the physician.

Unless otherwise defined, all technical and scientific terms used herein have the same meaning as commonly understood by one of ordinary skill in the art to which this invention belongs. Throughout the description and claims the word "comprise" and its variations, such as "comprising", are not intended to exclude other technical features, additives, components, or steps. The abstract of the application is incorporated herein. Additional objects, advantages and features of the invention will become apparent to those skilled in the art upon examination of the description or may be learned by practice of the invention. The following examples and drawings are provided by way of illustration, and are not intended to be limiting of the present invention.

DETAILED DESCRIPTION OF PARTICULAR EMBODIMENTS

Detailed Description of the Drawings

Figure 1A:
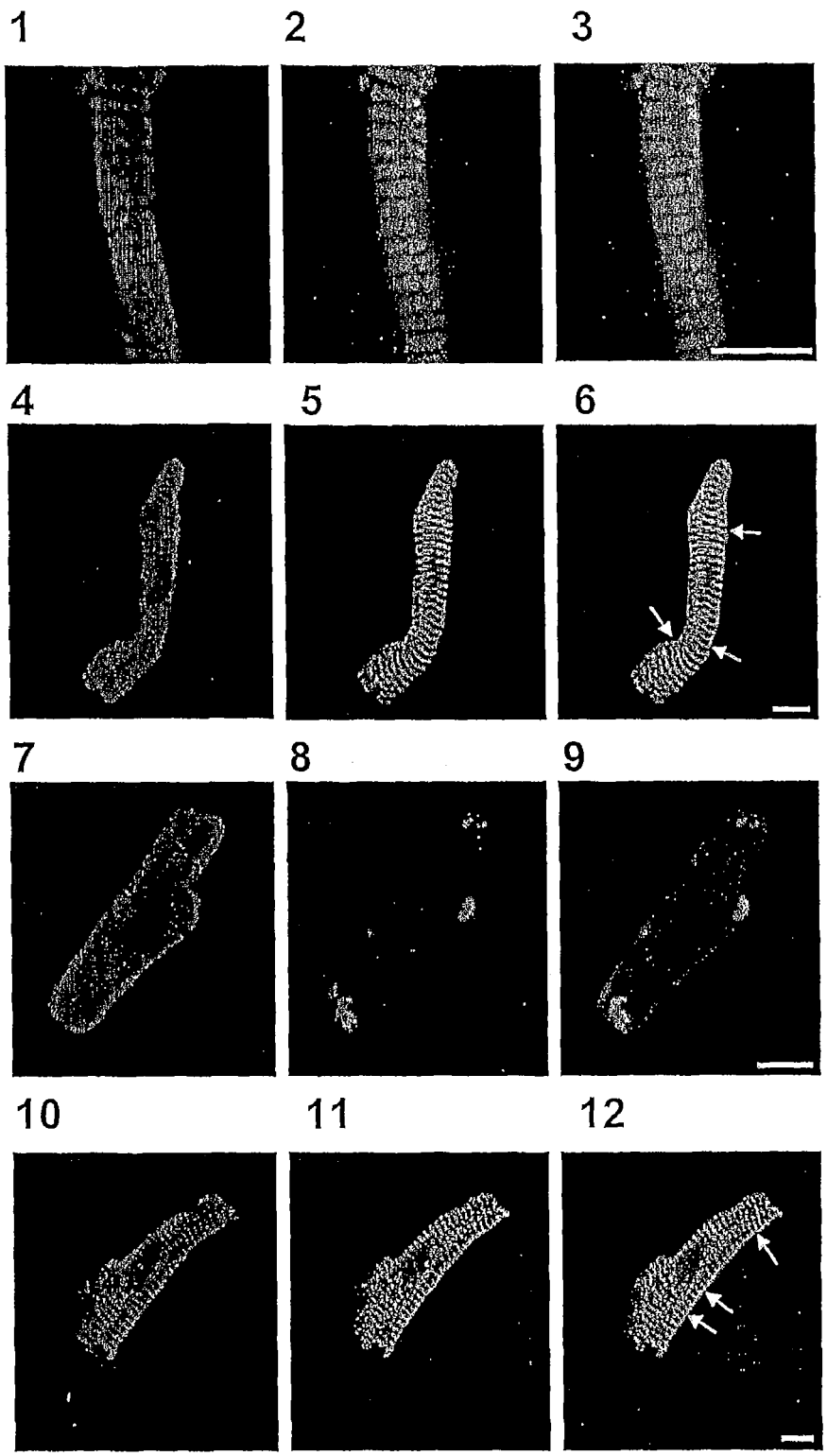
FIG. 1. Up-regulation of $A_{2A}$ receptor expression in patients with atrial fibrillation.
Figure 1B:
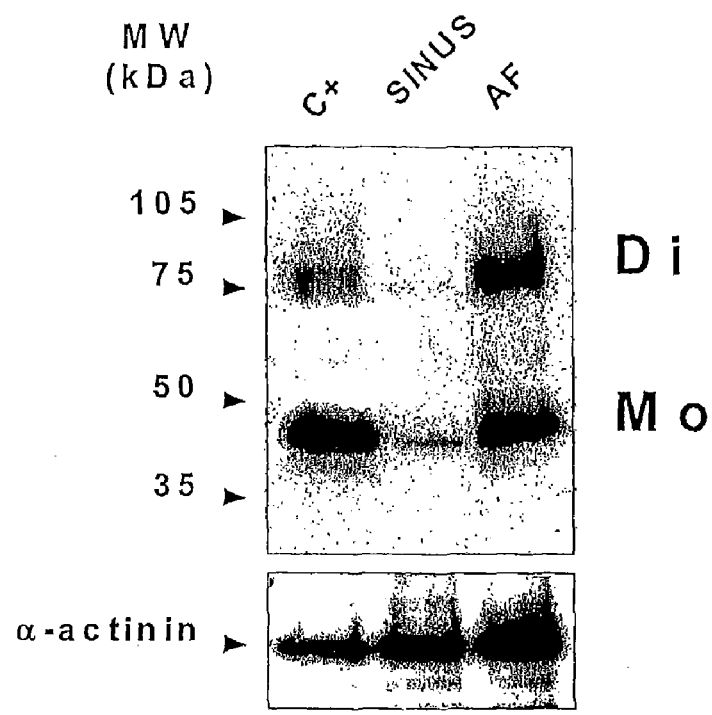
Figure 1C:
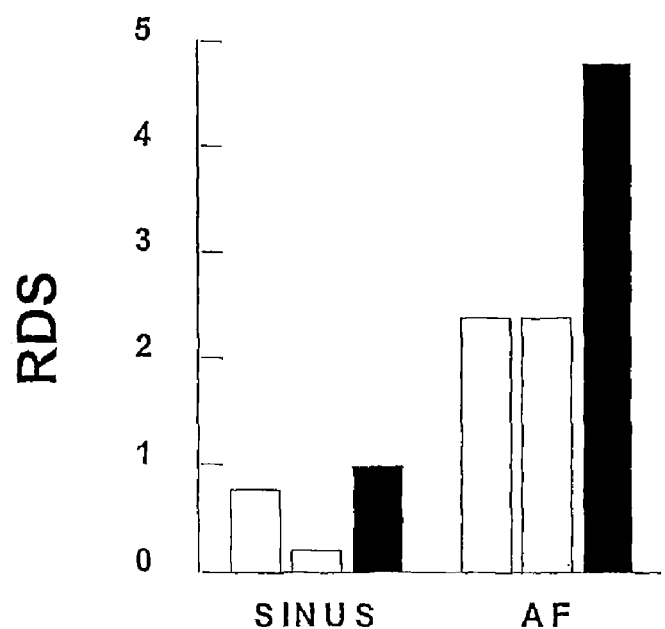

FIG. 1A shows freshly isolated human right atrial myocytes that were double stained with anti-$A_{2A}$ receptor (panels 1, 4, 7 and 10) and anti-myosin (2), anti-α-actinin (5), anti-connexin-43 (8) or anti-RyR (11). Superimposition of the double immunofluorescence images (panels 3, 6, 9 and 12) revealed colocalization of the $A_{2A}$ receptor with α-actinin and overlapping distribution of $A_{2A}$ receptor with the ryanodine receptor (RyR). FIG. 1B shows cell membranes from transiently transfected HEK cells with human $A_{2A}$ receptor (positive control, C+) and human atrial heart membranes obtained from individuals with sinus rhythm (SINUS) or with atrial fibrillation (AF) resolved by SDS-PAGE and immunoblotted using a rabbit anti-$A_{2A}$ receptor antibody. "Di" means dimer and "Mo" means monomer. FIG. 1C shows the Relative Densitometric Scan (RDS) of immunoblot of FIG. 1B. The total amount of $A_{2A}$ receptor (monomer plus dimer) is shown in black bars. Relative amounts of $A_{2A}$ receptor monomer (white bars) and dimer (grey bars) are normalized using the total sum of $A_{2A}$ receptor (dimer plus monomer) in each lane.

Figure 2A:
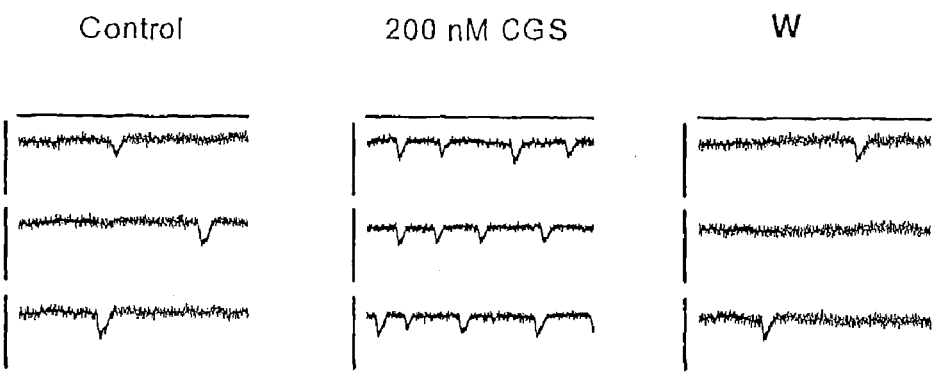
FIG. 2. Agonist stimulation of $A_{2A}$ receptor includes a PKA-dependent increase in spontaneous sarcoplasmic reticulum calcium release in patients with atrial fibrillation.
Figure 2B:
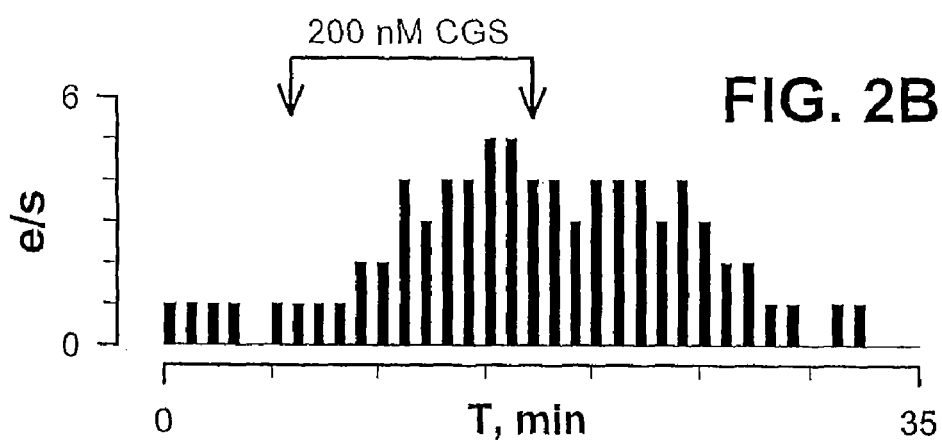
Figure 2C:
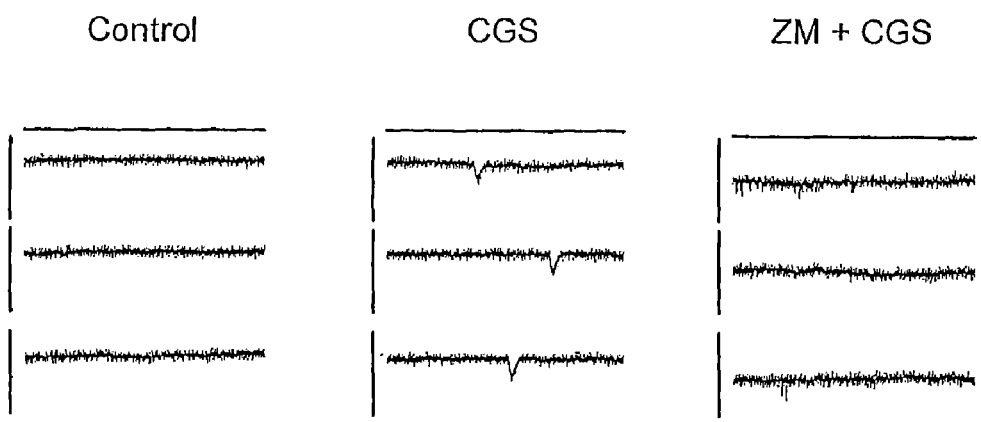
Figure 2D:
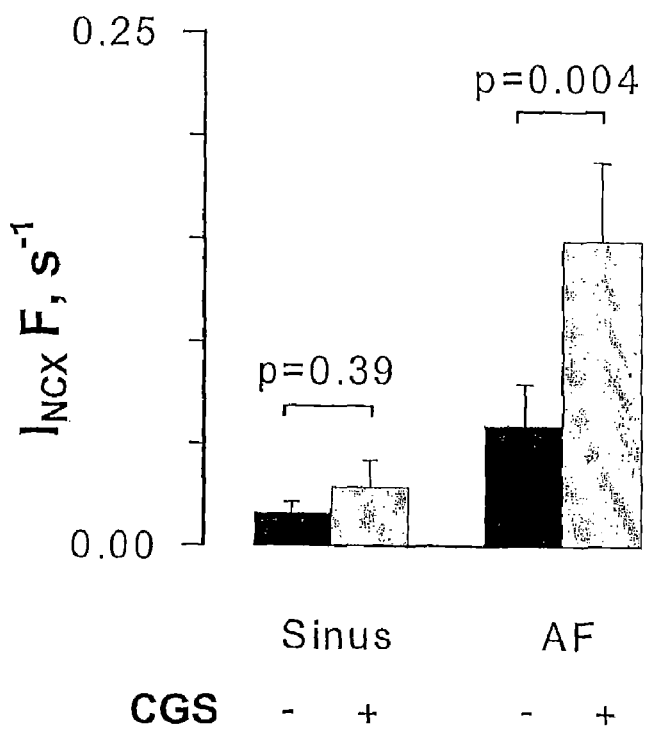
Figure 2E:
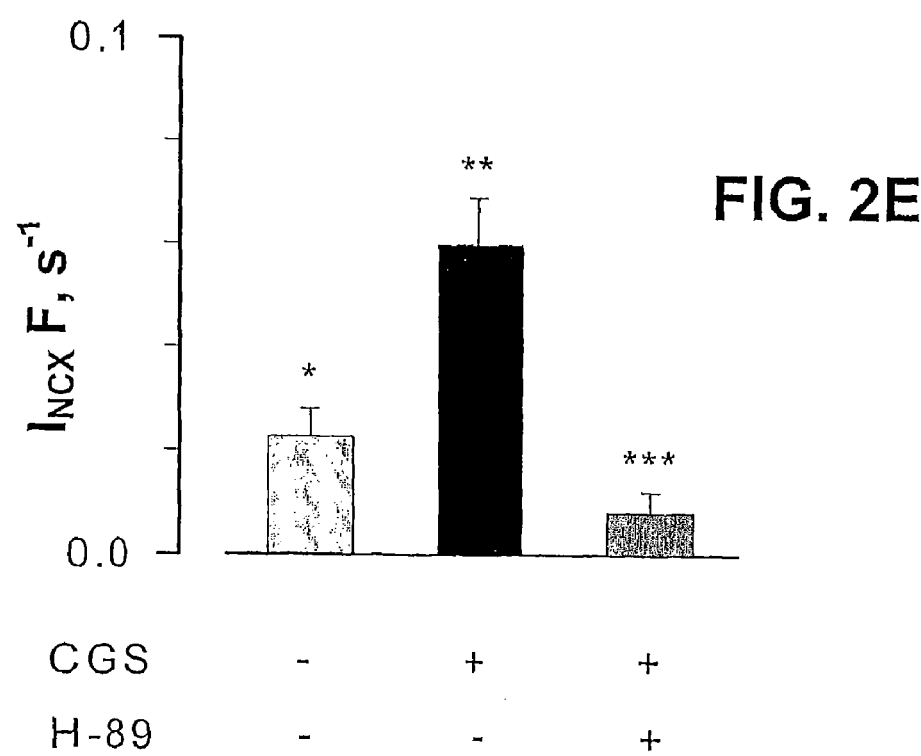

In FIG. 2A, spontaneous $I_{NCX}$ were recorded with the membrane potential clamped at −80 mV before (control), during (CGS) and after (wash, W) exposure of a myocardiocyte to 200 nM CGS 21680. Horizontal and vertical scale bars correspond to 30 s and 100 pA respectively. FIG. 2B shows time course of the stimulatory effect of CGS 21680 on the number of spontaneous Na—Ca exchange currents (counted as events on each 30 s sweep, e/s). The thick line above bars indicates the period of CGS 21680 application. FIG. 2C shows how the $A_{2A}$ antagonist ZM 241385 (1 μM) was able to revert the stimulatory effect of 200 nM CGS 21680 on spontaneous $I_{NCX}$. Horizontal and vertical scale bars correspond to 30 s and 100 pA respectively. FIG. 2D is a summary of the effect of CGS in cardiomyocytes from 8 control patients without and 11 patients with atrial fibrillation. Paired t-test was used to evaluate the effect of CGS 21680 and p-values are given above bars. $I_{NCX}$ F means $I_{NCX}$ frequency. FIG. 2E shows that the addition of 10 μM H-89 abolished the stimulatory effect of 200 nM CGS 21680 in 5 patients. ANOVA showed a significant effect of the treatment on the wave frequency (p=0.001) and post test gave p=0.03 for CGS vs. control, p=0.002 for CGS vs. CGS+H-89 and p=0.05 for CGS+89 vs. control.

Figure 3A:
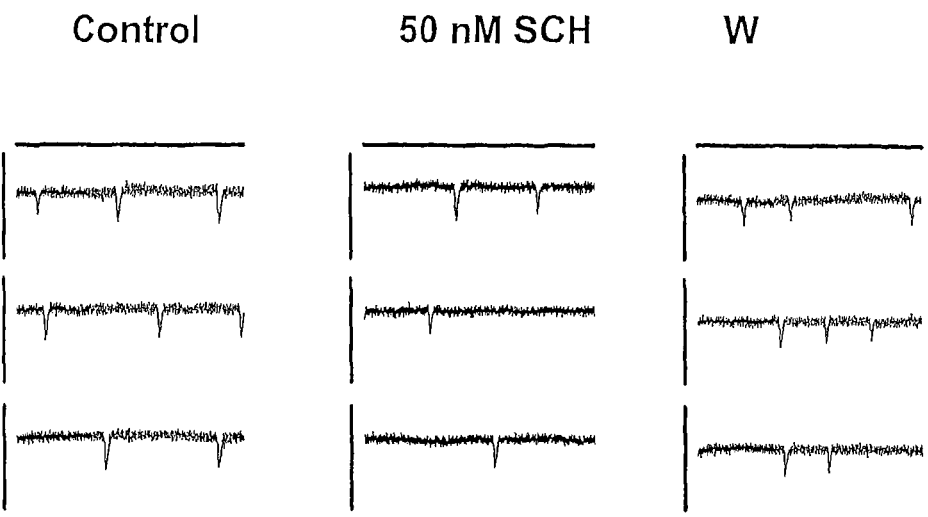
FIG. 3. $A_{2A}$ antagonists reduce basal spontaneous sarcoplasmic reticulum calcium release in patients with atrial fibrillation. Experiments showing spontaneous $I_{NCX}$ at a holding potential of −80 mV.
Figure 3B:
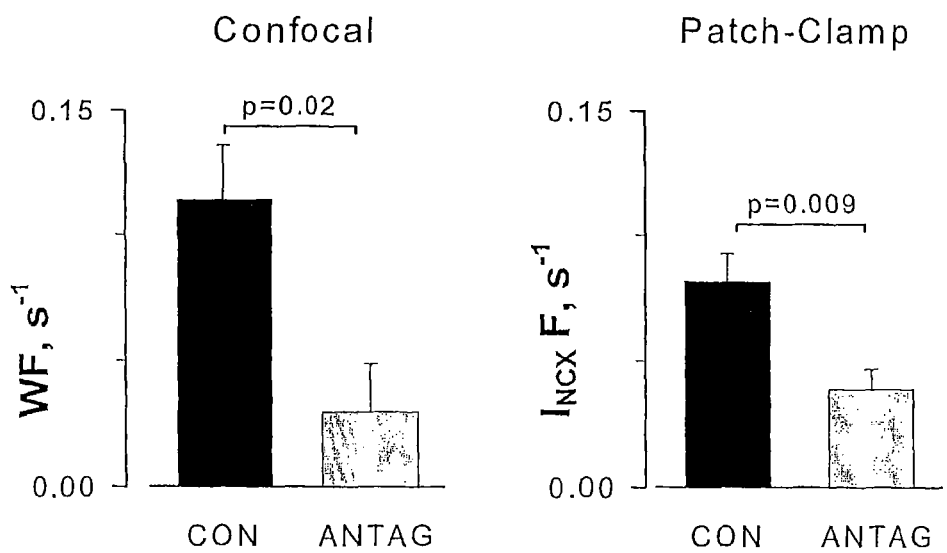

In FIG. 3A, the $A_{2A}$ antagonist SCH 58261 (50 nM) caused a reversible reduction of the spontaneous $I_{NCX}$ frequency in samples of patients with atrial fibrillation. Horizontal and vertical scale bars correspond to 30 s and 100 pA respectively. In FIG. 3B, $A_{2A}$ antagonists reduced both the spontaneous calcium wave frequency (WF) measured with confocal calcium imaging (left panel, n=6) or with patch-clamp technique (right panel, n=7). Effects of 50 nM of ZM 241385 and SCH 58261 were comparable and were pooled. Statistical significance using unpaired t-test for confocal experiments and paired t-test for patch-clamp experiments is given above bars.

Expression and Localization of $A_{2A}$ Receptor in Human Right Atrium

The presence of $A_{2A}$ receptor in human right atrial cardiomyocytes was investigated by immunoblotting. The results showed that $A_{2A}$ receptor was present in right atrium and that both monomeric and dimeric species of the receptor are expressed in this tissue, being the dimeric form minoritary in samples from atria in sinus rhythm. $A_{2A}$ receptor localization in atrial myocardium was studied by confocal microscopy in samples double labeled with antibodies against the receptor $A_{2A}$ and against either myosin, α-actinin, connexin-43 or the RyR. The $A_{2A}$ receptor was expressed following a transversal banded pattern along the myocardial fiber and co-localized with the cytoskeletal-associated protein α-actinin at the level of the Z line in the sarcomer. The distribution of $A_{2A}$ receptor was qualitatively similar in samples from patients with and without atrial fibrillation.

Up-Regulation of $A_{2A}$ Receptor Expression in Patients with Atrial Fibrillation Isolated atrial myocytes retained the $A_{2A}$ receptor banded pattern as well as the colonization with α-actinin and the overlapping distribution with RyR seen in the atrial tissue samples (cf. FIG. 1A). No differences in receptor localization were observed in cardiomyocytes from patients with and without atrial fibrillation (data not shown). $A_{2A}$ receptor protein level, measured by western blotting, were markedly increased in patients with atrial fibrillation (cf. FIG. 1B-C) and interestingly the dimeric $A_{2A}$ receptor species, which is the functional form present on the cell surface, was markedly elevated in atrial fibrillation (cf. FIG. 1C). No significant differences were observed in blood vessels. Therefore, these results not only demonstrated for the first time the expression of $A_{2A}$ receptor in human atrial myocytes, but also their up-regulation, mainly in the homodimeric form, in patients with atrial fibrillation.

Agonist Stimulation of $A_{2A}$ Receptor Induces a PKA-Dependent Increase in Spontaneous Sarcoplasmic Reticulum (SR) Calcium Release in Patients with Atrial Fibrillation The effect of $A_{2A}$ receptor agonists on spontaneous SR calcium release was analyzed in isolated atrial myocytes from patients in sinus rhythm and in patients with atrial fibrillation. Both local non-propagating calcium release (calcium sparks) and regenerative calcium release from the SR (calcium waves) were analyzed. Preincubation with the $A_{2A}$ receptor agonist CGS 21680 (200 nM), increased the number of calcium waves in patients with atrial fibrillation but not in those without the arrhythmia.

To determine whether the effect of CGS 21680 on spontaneous SR calcium release is secondary to an effect on the membrane potential, patch-clamp technique was used to clamp the membrane potential at −80 mV. This did not impede that CGS 21680 reversibly increased the number of spontaneous calcium waves measured as the Na—Ca exchange current ($I_{NCX}$) activated by them (cf. FIGS. 2A and B). Indeed, this approach confirmed the significant stimulatory effect of CGS 21680 in atrial fibrillation patients (cf. FIG. 2D). Therefore, the increased spontaneous SR calcium release induced by CGS 21680 is due to an $A_{2A}$ receptor-dependent regulation of the RyR activity. The specific effect of CGS 21680 was reversed by the two selective $A_{2A}$ antagonists ZM 241385 (cf. FIG. 2C) and SCH 58261.

Since $A_{2A}$ receptor is coupled to Gs proteins, agonist-mediated receptor activation should increase cAMP levels, which in turn leads to PKA activation and RyR phosphorylation. To test whether $A_{2A}$ receptor exerts its effect through a cAMP-dependent activation of PKA, the selective PKA inhibitor H-89 was employed. The stimulatory effect of CGS 21680 in myocytes from patients with atrial fibrillation was eliminated by H-89 (cf. FIG. 2E), confirming that $A_{2A}$ receptor-dependent regulation of spontaneous SR calcium release is in fact mediated by PKA activation. Interestingly, H-89 not only abolished the effect of CGS 21680 but it actually reduced spontaneous calcium release to a significantly lower level than the baseline recorded before CGS 21680 application. Analysis of calcium sparks and waves with confocal microscopy confirmed the PKA dependency of $A_{2A}$ receptor-mediated spontaneous calcium release.

$A_{2A}$ Receptor Blockade Reduces Basal Spontaneous SR Calcium Release

The existence of a basal cAMP tone in human atrial myocytes has been claimed in studies of the neuro-hormonal modulation of the L-type calcium currents. The observation of the inventors that the PKA blocker H-89 reduces the calcium wave frequency below baseline level further suggests that there is a basal $A_{2A}$ receptor-dependent cAMP tone in human atrial myocytes. In agreement with this notion, $A_{2A}$ receptor selective antagonists SCH 58261 or ZM 241385 applied to cells from atrial fibrillation patients showing an elevated basal SR calcium release, significantly reduced the calcium wave frequency measured either by confocal microscopy or by patch clamp technique (cf. FIG. 3).

Human Samples

Cardiac tissue samples from a total of 54 patients undergoing cardiac surgery were used in this study. Although the atrial tissue samples consisted of tissue that would normally be discarded during surgery, permission to be used in this study was obtained from each patient. The study was approved by the Ethical Committee of Sant Pau Hospital (Barcelona, Spain).

Seventeen out of the 54 patients had a history of atrial fibrillation while the remaining patients were free of this arrhythmia. Twenty-five patients had no atrial fibrillation but did have left atrial dilation (left atrial diameter >40 mm). The number of patients used in specific experimental series is indicated where appropriate. Patients treated with $Ca^{2+}$ antagonists were excluded from the study. Other patient medication was not found to significantly influence the parameters measured. For immunohistochemical analysis a total of 8 patients with atrial fibrillation (left atrial diameter: 53.8±6.8 mm), and 15 patients without atrial dilation and no history of atrial fibrillation were serving as controls (left atrial diameter: 36.5±3.4 mm).

Antibodies

The following primary antibodies were used: Rabbit affinity purified anti-$A_{2A}$ receptor polyclonal antibody VC21-Ab developed against a peptide corresponding to the second extracellular loop of $A_{2A}$ receptor; rabbit anti-$A_{2A}$ receptor antibody (Clone PA1-042, Affinity BioReagents, Golden, Colo., U.S.A.); mouse Anti-Slow muscle myosin antibody (Clone NOQ7.5.4D, Chemicon International, Temecula, Calif., U.S.A.); mouse anti-α-actinin antibody (Clone EA-53, SigmaAldrich Chemical Co., St. Louis, Mo., U.S.A.); mouse anti-connexin-43 antibody (Clone 2, Transduction Laboratories, Lexington, Ky., U.S.A.); mouse anti-ryanodine receptor antibody (Clone C3-33, Calbiochem, San Diego, Calif., U.S.A.). The secondary antibodies used were: ALEX-AFLUOR 488®-conjugated goat anti-mouse IgG (1/1000), TEXAS RED®-conjugated goat anti-rabbit IgG (1/2000) (Molecular Probes, Eugene, Oreg., U.S.A.) horseradish-peroxidase conjugated goat anti-rabbit IgG (1/60000) (Pierce Chemical Co., Rockford, Ill., U.S.A.) and rabbit anti-mouse IgG (1:2000) (Dako, Glostrup, Denmark).

Myocytes Isolation

Myocytes were isolated from human atrial tissue samples as previously described (cf. L. Hove-Madsen et al., "Atrial fibrillation is associated with increased spontaneous calcium release from the sarcoplasmic reticulum in human atrial myocytes", *Circulation* 2004, vol. 110, pp. 1358-63). Briefly, the samples were rinsed, cut into small pieces in a calcium free solution containing 30 mM butanedione monoxime (BDM), and incubated at 35° C. in a $Ca^{2+}$ free solution containing 0.5 mg/ml collagenase (Worthington type 2, 318 u/mg) and 0.5 mg/ml proteinase (Sigma type XXIV, 11 u/mg solid). After 45 minutes, the tissue was removed from the enzyme solution and cells were disgregated in $Ca^{2+}$-free solution with a Pasteur pipette. The remaining tissue was digested for 3×15 minutes in a fresh calcium free solution containing 0.4 mg/ml collagenase. Solutions containing disgregated cells were centrifuged at 600 rpm for 1 min, resuspended in calcium-free solution and then calcium was gradually increased to 1 mM. Only elongated cells with clear cross striations and without granulation were used for experiments.

Positive Control: Cell Culture and Transfection

HEK-293 cells were grown in Dulbecco's modified Eagle's medium (DMEM, Sigma Aldrich Chemical Co.). Cells were transiently transfected with the DNA encoding for human $A_{2A}$ receptor (cf. M. Canals et al. "Adenosine $A_{2A}$-dopamine $D_2$ receptor-receptor heteromerization: qualitative and quantitative assessment by fluorescence and bioluminescence energy transfer", *J. Biol. Chem.* 2003, vol. 278, pp. 46741-9) by calcium phosphate precipitation. The cells were harvested at either 24 or 48 hours after transfection.

Spontaneous SR Calcium Release

Calcium sparks and calcium waves were detected in fluo-3 loaded cells using a laser-scanning confocal microscope (Leica TCS SP2 AOBS, Germany). The experimental solution contained (in mM): NaCl 136, KCl 4, $NaH_2PO_4$ 0.33, $NaHCO_3$ 4, $CaCl_2$ 2, $MgCl_2$ 1.6, HEPES 10, Glucose 5, pyruvic acid 5, (pH=7.4). Fluorescence emission was collected between 500 and 650 nm with the excitation at 488 nm attenuated to 1-5%. Calcium sparks and calcium waves were measured at resting conditions during 2×10.24 s, at a scan rate of 1 kHz. Calcium sparks were detected as an increase in the signal mass of a 3 μm section through the center of a calcium spark, without any detectable increase in an adjacent 3 μm section. An increase in the signal mass in two or more adjacent 3 μm sections were counted as calcium waves. The amplitude of each calcium spark and its half-life were determined from an exponential fit of the decaying phase of the calcium spark transient. The calcium spark frequency was determined for each cell and normalized to the scanned cell length.

Patch-Clamp

The transient inward Na—Ca exchange current associated with calcium waves was recorded in the perforated patch configuration using a software controlled patch-clamp amplifier (EPC 10, HEKA, Germany). The pipette resistance was 1.5-4 MΩ. Experiments were carried out at room temperature and began when the access resistance was stable and had decreased to less than 5 times the pipette resistance. The extracellular solution contained (in mM): NaCl 127, tetraethyl ammonium (TEA) 5, HEPES 10, $NaHCO_3$ 4, $NaH_2PO_4$ 0.33, glucose 10, pyruvic acid 5, $CaCl_2$ 2, $MgCl_2$ 1.8, (pH=7.4). The pipette solution contained (in mM): aspartic acid 109, CsCl 47, $Mg_2ATP$ 3, $MgCl_2$ 1, $Na_2$phosphocreatine 5, $Li_2GTP$ 0.42, HEPES 10 and 250 μg/ml amphotericin B, (pH=7.2). The $A_{2A}$ receptor agonist CGS 21860, the antagonists ZM 241385 and SCH 58261, and the protein kinase A inhibitor H-89 were all dissolved in DMSO and kept as 10 mM stock solutions. The caffeine releasable SR calcium content was measured by transiently exposing cells to 10 mM caffeine. The time integral of the resulting Na—Ca exchange current was converted to pmoles ($10^{-18}$ mol) of calcium released from the SR assuming a stoichiometry of $3Na^+$: $1Ca^{2+}$ for the Na—Ca exchanger.

Data Analysis and Statistics

Electrophysiological and confocal calcium imaging experiments were carried out without knowledge about the clinical data of the patients. The $Ca^{2+}$ sparks and $Ca^{2+}$ waves recorded in cells from the same patient were averaged. Unless otherwise stated, average values from each patient were used for statistical analysis and expressed as mean±S.E.M. Data sets were tested for normality. Student's t-test was used to assess significant differences when testing a specific effect. ANOVA was used for comparison of multiple effects and Student-Newman-Keuls post test was used to evaluate the significance of specific effects.

Membrane Preparation

Membranes were obtained by centrifugation after disruption of cells with a Polytron homogenizer (Kinematica, PTA 20TS rotor, setting 5, three 15 s periods) in ice-cold solution of 0.32 M sucrose containing 5 mM Tris-HCl (pH 7.4; buffer A). Cell debris was separated by centrifugation at 1000×g for 30 min at 4° C. (3500 rpm in Type 75Ti rotor). The supernatant was centrifuged at 26000×g for 30 min at 4° C. (20000 rpm in Type 75Ti rotor) and pellet was resuspended in buffer A, incubated at 37° C. for 30 min and centrifuged at the same conditions. Pellet was resuspended in 0.3 M KCl, stirred at 4° C. overnight, centrifuged at 26000×g for 30 min at 4° C. (20000 rpm in Type 75Ti rotor) and washed once with buffer A as described above. Final pellet (membrane fraction) was resuspended in 50 mM Tris-HCl and frozen at −80° C. Membrane suspensions from transfected HEK cells were obtained as described previously (cf. C. Herrera, et al., "Adenosine $A_{2B}$ receptors behave as an alternative anchoring protein for cell surface adenosine deaminase in lymphocytes and cultured cells", *Mol. Pharmacol.* 2001, vol. 59, pp. 127-34). Protein was quantified by the bicinchoninic acid method (Pierce Chemical Co.)

Gel Electrophoresis and Immunoblotting

Membranes from human cells or transiently transfected HEK cells were treated with SDS-PAGE sample buffer (8 M urea, 2% SDS, 100 mM DTT, 375 mM Tris, pH 6.8) by heating at 37° C. during 2 h and resolved by SDS-polyacrylamide gel electrophoresis in 10% gels. Proteins were transferred to PVDF membranes using a semi-dry transfer system and immunoblotted with the indicated antibody and then horseradish-peroxidase (HRP)-conjugated goat anti-rabbit IgG (1/60,000). The immunoreactive bands were developed using a chemiluminescent detection kit (SuperSignal, West Pico Chemiluminiscent substrate, Pierce).

Immunostaining

For immunohystochemistry, human atrial tissue was embedded in OCT and frozen in liquid nitrogen-cooled isopentane. Eight micrometer sections were cut on a cryostat cooled to 18° C. Sections were collected onto SUPERFROST PLUS® (BDH Chemicals Ltd., Poole, United Kingdom) slides, air dried and stored at −70° C. For immunofluorescence, sections were blocked for 30 min in 10% donkey serum in Tris-buffered saline (TBS) (150 mM NaCl/50 mM Tris-HCl, pH 7.5). Slides were incubated with affinity purified anti-$A_{2A}$ receptor (VC21, 25 μg/ml) and with anti-α-actinin (1:500 dilution), anti-myosin (2 μg/ml), anti-connexin-43 (2.5 μg/ml) and anti-ryanodine receptor (6.5 μg/ml) for one hour at room temperature and then washed three times for 10 min in TBS. ALEXA FLUOR 488® conjugated goat anti-mouse IgG and TEXAS RED®-conjugated goat anti-rabbit IgG were applied in blocking solution at a dilution of 1:2000. Section were rinsed and mounted with VECTASHIELD® immunofluorescence medium (Vector Laboratories Inc., Burlingame, Calif., U.S.A.). For immunocytochemistry, freshly isolated human cardiac myocytes were plated in 24 mm glass coverslips coated with poly-D-lysine. After adhesion, isolation solution cells were rinsed in phosphate-buffered saline and were fixed with 2% paraformaldehyde in PBS for 20 min at room temperature. Cells were washed with PBS and were incubated with 0.1 M glycine for 5 min to quench the aldehyde groups. After washing with PBS, myocytes were permeabilized with 0.2% Triton-X-100 in PBS for 15 min. Cells were then washed with PBS, blocked for 30 min with 10% horse serum at room temperature and incubated with the next primaries antibodies: rabbit polyclonal anti-$A_{2A}$ receptor (10 μg/ml), anti-α-actinin (1:500 dilution), anti-myosin (1:500 dilution) and anti-connexin-43 (1:150 dilution) for one hour at room temperature, washed three times with PBS and where stained with anti-mouse antibody conjugated to ALEXA FLUOR 488® and/or anti-rabbit conjugated to TEXAS RED®. Finally cells were rinsed again for three times and mounted with VECTASHIELD®. Confocal microscopic observations were made with a Leica TCS 4D confocal laser scanning microscope (Leica Lasertechnik GmbH, Heidelberg, Germany).

The invention claimed is:

1. A method of treating atrial fibrillation in a mammal, comprising administering to said mammal an effective amount of a selective adenosine $A_{2A}$ receptor antagonist, wherein the selective adenosine $A_{2A}$ receptor antagonist is a compound selected from the group consisting of:

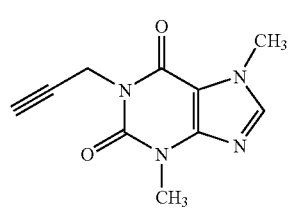

(1)

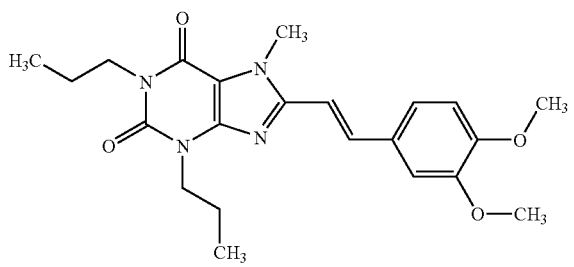

(2)

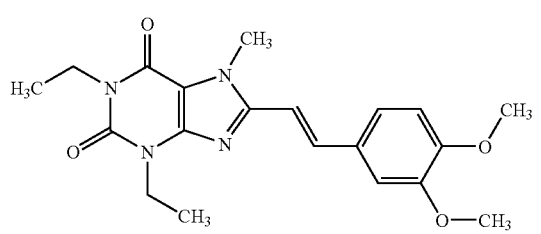

(3)

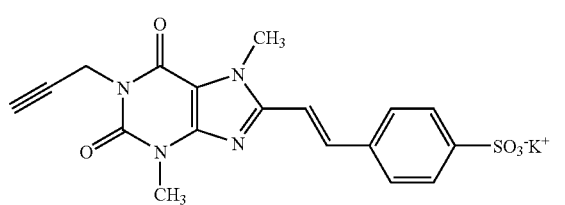

(4)

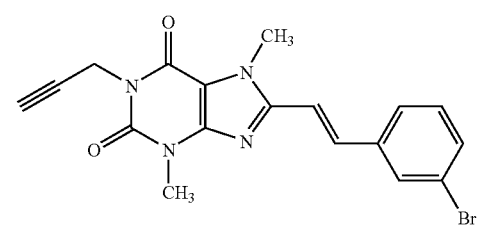

(5)

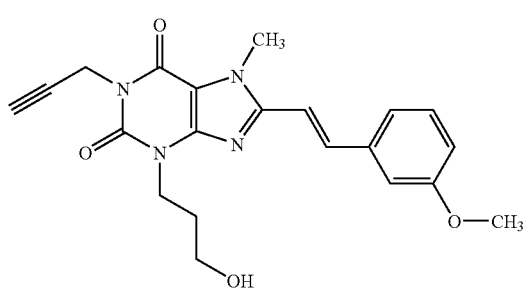

(6)

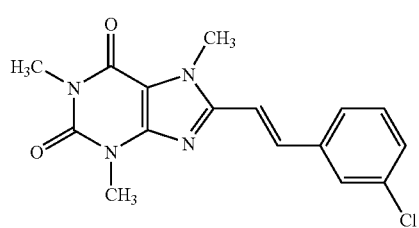

(7)

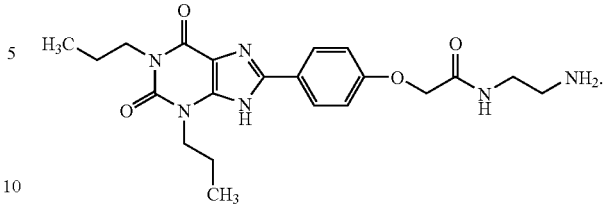

(8)

2. The method according to claim 1, wherein the selective adenosine $A_{2A}$ receptor antagonist is the compound of formula (3).

3. The method according to claim 1, wherein the selective adenosine $A_{2A}$ receptor antagonist is the compound of formula (6).

4. The method according to claim 1, wherein the selective adenosine $A_{2A}$ receptor antagonist is the phosphoric acid ester of the compound of formula (6).

5. The method of claim 1, wherein said mammal is a human.

6. A method of treating atrial fibrillation in a mammal, comprising administering to said mammal an effective amount of a selective adenosine $A_{2A}$ receptor antagonist, wherein the selective adenosine $A_{2A}$ receptor antagonist is a compound selected from the group consisting of:

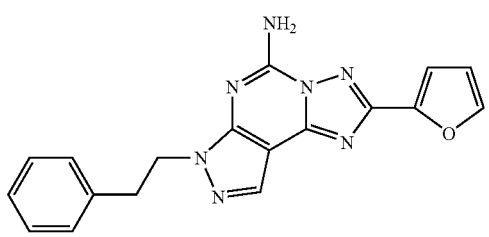

(9)

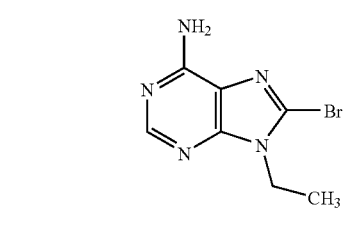

(10)

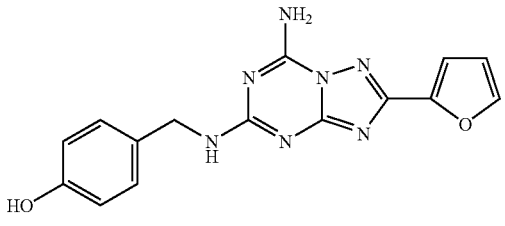

(11)

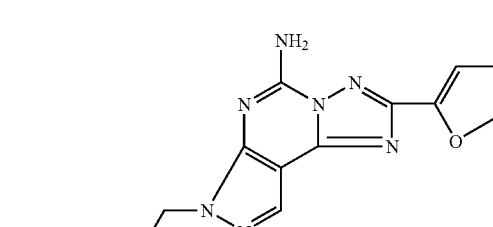

(12)

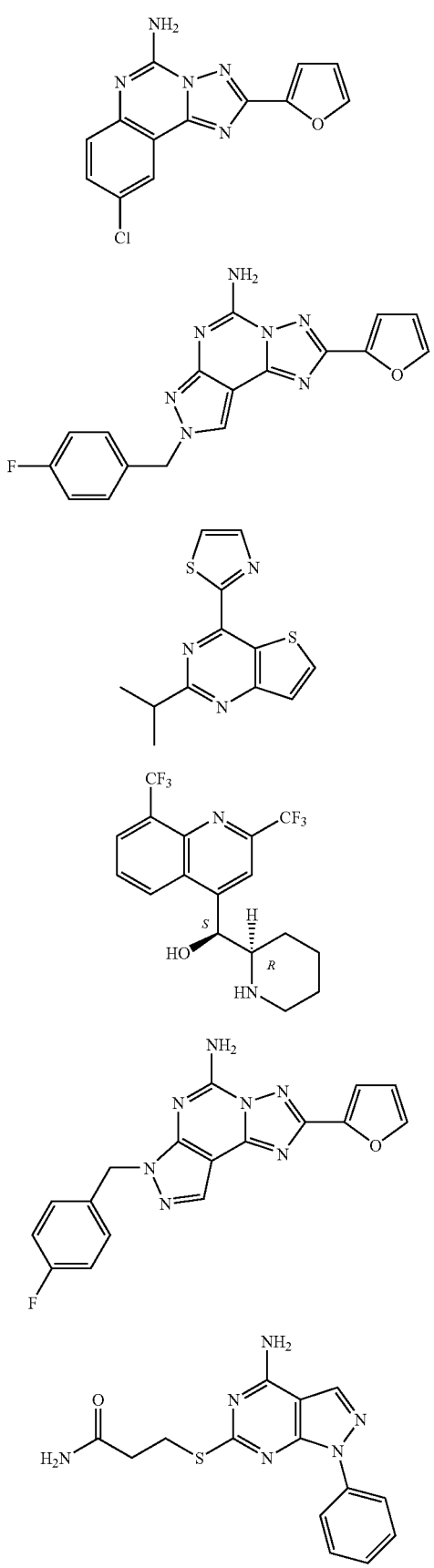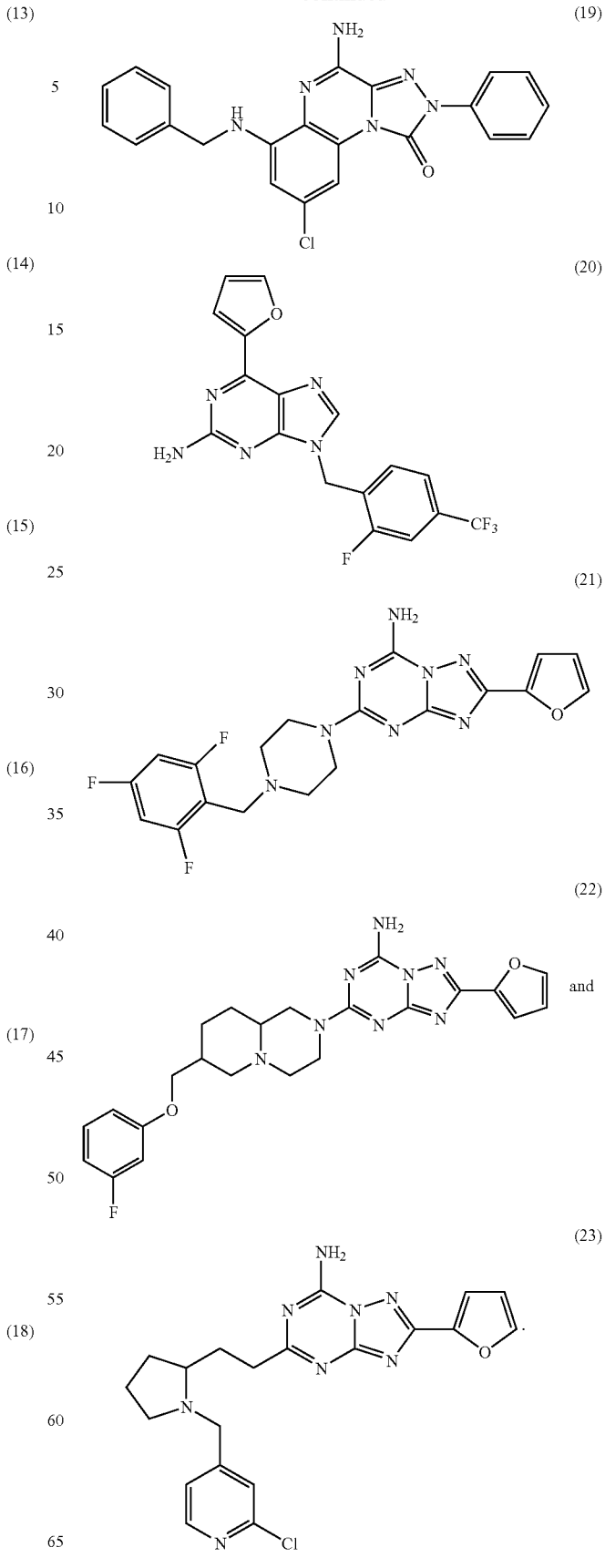

7. The method according to claim 6, wherein the selective adenosine $A_{2A}$ receptor antagonist is the compound of formula (15).

8. The method of claim 6, wherein said mammal is a human.

* * * * *